(12) United States Patent
Savolainen et al.

(10) Patent No.: US 9,682,903 B2
(45) Date of Patent: Jun. 20, 2017

(54) PROCESS FOR SEPARATION AND PURIFICATION OF RENEWABLE PROPANE

(71) Applicant: Neste Oyj, Espoo (FI)

(72) Inventors: Pekka Savolainen, Helsinki (FI);
Rogier Van De Velde, Rockanje (NL);
Martijn Van Den Berg, Hoogvliet Rt (NL); Juha Visuri, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/189,419

(22) Filed: Jun. 22, 2016

(65) Prior Publication Data

US 2017/0081262 A1   Mar. 23, 2017

(30) Foreign Application Priority Data

Sep. 18, 2015   (FI) ..................................... 20155672

(51) Int. Cl.
| | |
|---|---|
| *B01D 53/22* | (2006.01) |
| *C07C 7/04* | (2006.01) |
| *C07C 7/144* | (2006.01) |
| *C01B 3/50* | (2006.01) |
| *F25J 3/02* | (2006.01) |
| *C07C 7/00* | (2006.01) |
| *C07C 7/11* | (2006.01) |
| *C01B 3/52* | (2006.01) |

(52) U.S. Cl.
CPC ............ *C07C 7/005* (2013.01); *B01D 53/229* (2013.01); *C01B 3/503* (2013.01); *C01B 3/52* (2013.01); *C07C 7/04* (2013.01); *C07C 7/11* (2013.01); *C07C 7/144* (2013.01); *F25J 3/0242* (2013.01); *F25J 3/0247* (2013.01); *F25J 3/0252* (2013.01); *C01B 2203/0405* (2013.01); *C01B 2203/048* (2013.01); *C01B 2203/0415* (2013.01); *C01B 2203/0475* (2013.01); *C01B 2203/0485* (2013.01); *F25J 2205/30* (2013.01); *F25J 2205/40* (2013.01); *F25J 2205/80* (2013.01); *F25J 2215/10* (2013.01); *F25J 2215/64* (2013.01); *F25J 2245/02* (2013.01); *F25J 2290/12* (2013.01)

(58) Field of Classification Search
CPC .............. B01D 53/229; B01D 53/1468; B01D 53/1475; C07C 7/005; C07C 7/04; C07C 7/144; C01B 3/501; C01B 3/505; C01B 2203/0405; C01B 3/503; F25J 3/0242; F25J 3/0247; F25J 3/0252; F25J 2205/40; F25J 2205/80; F25J 2215/10; F25J 2215/64

See application file for complete search history.

(56) References Cited

U.S. PATENT DOCUMENTS

| | | | | |
|---|---|---|---|---|
| 4,842,718 | A | * | 6/1989 | Luteijn ................... C07C 7/144 208/103 |
| 5,082,481 | A | * | 1/1992 | Barchas ................. F25J 3/0252 62/624 |

(Continued)

FOREIGN PATENT DOCUMENTS

| | | |
|---|---|---|
| EP | 1 741 768 | 1/2007 |
| WO | WO 99/45036 | 9/1999 |

(Continued)

*Primary Examiner* — Jason M Greene
(74) *Attorney, Agent, or Firm* — Leason Ellis LLP

(57) ABSTRACT

A method for treating a gas stream comprising hydrogen and propane, where a combination of membrane separation and elevated pressure distillation is used to separate the hydrogen gas from the propane gas.

18 Claims, 1 Drawing Sheet

(56) References Cited

U.S. PATENT DOCUMENTS

| | | | |
|---|---|---|---|
| 5,979,178 A * | 11/1999 | Engler | C07C 7/144 |
| | | | 62/624 |
| 6,271,319 B1 | 8/2001 | Baker et al. | |
| 6,361,582 B1 * | 3/2002 | Pinnau | B01D 71/52 |
| | | | 95/45 |
| 8,318,996 B2 | 11/2012 | Murty et al. | |
| 2003/0033929 A1 * | 2/2003 | Pinnau | B01D 53/228 |
| | | | 95/45 |
| 2005/0005765 A1 * | 1/2005 | Siadous | B01D 53/229 |
| | | | 95/45 |
| 2006/0266213 A1 | 11/2006 | Riu et al. | |
| 2008/0207975 A1 * | 8/2008 | Crone | C07C 7/04 |
| | | | 585/655 |
| 2010/0077796 A1 * | 4/2010 | Gadre | B01D 53/229 |
| | | | 62/620 |
| 2011/0290110 A1 * | 12/2011 | Zhou | B01D 53/229 |
| | | | 95/45 |
| 2012/0029252 A1 * | 2/2012 | Lissianski | C10B 19/00 |
| | | | 585/240 |
| 2012/0047793 A1 | 3/2012 | Murty et al. | |
| 2012/0190904 A1 * | 7/2012 | Butler | C01B 3/503 |
| | | | 585/440 |
| 2014/0144321 A1 * | 5/2014 | Sawamura | B01D 53/229 |
| | | | 96/4 |

FOREIGN PATENT DOCUMENTS

| | | |
|---|---|---|
| WO | WO 99/67587 | 12/1999 |
| WO | WO 2013/148906 | 10/2013 |

* cited by examiner

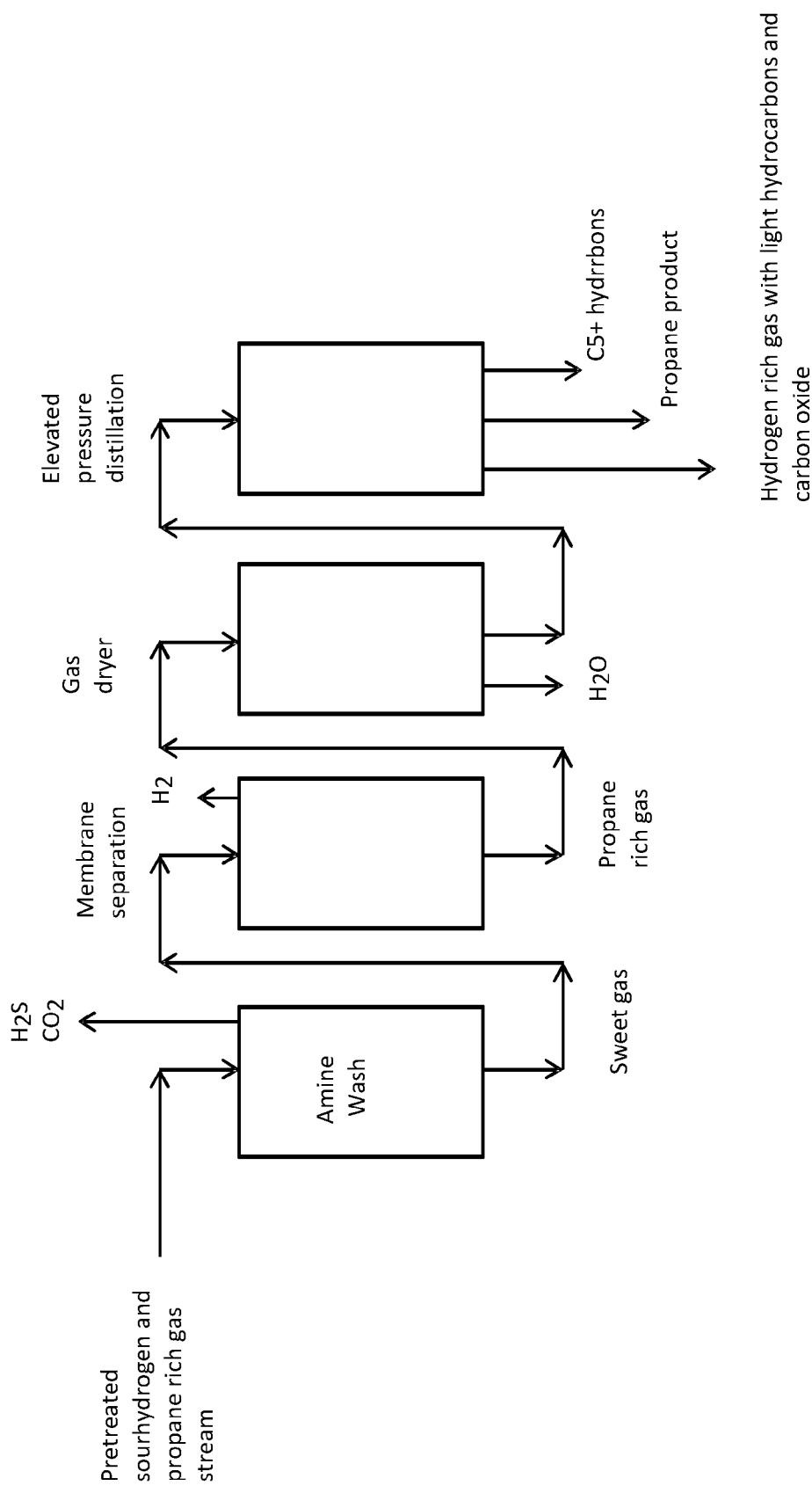

PROCESS FOR SEPARATION AND PURIFICATION OF RENEWABLE PROPANE

CROSS-REFERENCE TO RELATED APPLICATIONS

The present application claims priority under 35 U.S.C. §119 to Finish Patent Application No. 20155672, filed Sep. 18, 2015, which is hereby incorporated by reference in its entirety.

TECHNICAL FIELD

The present invention relates to methods for treating gas streams comprising hydrogen and propane, more specifically methods for treating reactor outlet gasses generated from the hydrotreatment, such as hydrodeoxygenation of renewable feed sources, in particular glyceridic and/or glycerol containing feed sources.

BACKGROUND

Renewable fuels are fuels produced from renewable resources. Such fuels include biodiesel. One potential feedstock source for preparing biodiesel is to use a feedstock that contains glycerides, which are present in many renewable feed sources, including many vegetable oils and animal fats. This feedstock typically contains triglycerides as well as amounts of di- and monoglycerides. Typical triglycerides have a glycerol backbone with up to three long-chain fatty acids covalently bound to the glycerol backbone through an ester linkage. The glycerol backbone may be separated from the fatty acids, and the fatty acids may have a carbon chain length that is suitable for use, typically after further processing, as for example fuels, additives, and lubricants. Often the glyceride feedstock undergoes catalytic deoxygenation under hydrogen pressure, which provides hydrocarbons with a chain length suitable for use as fuels or lubricants, as well as propane and/or propylene from the glycerol backbone.

WO 2013/148906 (to ExxonMobil Research and Engineering Company) relates to the processing of feeds containing triglycerides from renewable sources to produce an olefinic diesel fuel product and propylene. It is described in [0086]-[0089] that propylene can be separated from gas phase components, which may include $H_2O$, $CO_2$, CO, $H_2$, $H_2S$, $N_2$, light ends and propane. It involves separation of the gas phase products from the liquid products from the deoxygenation reaction. Propylene is then separated from the remaining gas phase components. Cryogenic distillation columns are indicated as being beneficial for separation of propane from propylene, and it is suggested that another option for separating propylene from the gas phase mixture could be to use a gas separation train similar to the separation used in some fluid catalytic cracking reaction systems.

U.S. Pat. No. 8,318,996 B2 (to UOP LLC) relates to methods for treating a hydrogen recycle gas in a process for converting biorenewable feedstock into green diesel comprising removing light hydrocarbons from the hydrogen recycle gas by contacting the hydrogen recycle gas with a sponge oil. Propane is then recovered from a propane-rich sponge oil by a propane fractionation unit.

Thus, there remains a need for further methods that can separate at least propane from hydrogen.

SUMMARY OF INVENTION

The object of the present invention is to provide a method and a plant that can separate at least propane from hydrogen in a manner that maximises hydrogen recovery and at the same time reduce the footprint and/or energy consumption of such method and plant carrying out the method.

To solve the problem, the present invention provides a method for treating a gas stream comprising hydrogen and propane, comprising the steps of: a) providing a membrane having a feed side and a permeate side, the membrane being selective for hydrogen over propane; b) passing the gas stream across the feed side of the membrane; c) withdrawing from the feed side a retentate stream depleted in hydrogen and enriched in propane compared with the gas stream; d) withdrawing from the permeate side a permeate stream enriched in hydrogen and depleted in propane compared with the gas stream; e) subjecting the retentate stream to elevated pressure distillation to separate hydrogen from propane.

That is, the inventors of the present invention in a first aspect of the invention found that the combination of a membrane separation, where the membrane is permeable to hydrogen over propane, with an elevated pressure distillation unit for separation of hydrogen from propane provides a two-fold separation of hydrogen from propane, first in the membrane, and later in the elevated pressure distillation. The membrane separation reduces the volume of gas that has to be separated in the elevated pressure distillation step which allows a reduction in the dimensions and energy consumption of the elevated pressure distillation unit due to the lower volume and higher dew point temperature of gas that has to be treated. Additionally, the combination of a membrane separation unit, the membrane permeable to hydrogen over propane, with an elevated pressure distillation unit enables the recovery in an energy efficient way of both hydrogen and propane, the latter being present in a significant volume compared to refining of diesel oil from non-glyceride feedstocks, e.g. crude distillation.

The membrane being selective for hydrogen over propane may exhibit a selectivity for hydrogen over propane of at least 5.

The gas stream may further comprise at least one further gas chosen from the group consisting of: $H_2O$, $CO_2$, CO, $H_2S$, $NH_3$ and light hydrocarbons. Carbon oxides (e.g. CO and $CO_2$) are often present in gas streams from processing of renewable feedstock.

The retentate stream may be subjected to one or more supplementary treatment steps to remove at least a portion of the at least one further gas before being subjected to the elevated pressure distillation.

When the gas stream at least further comprises $CO_2$ and/or $H_2S$, the gas stream may be subjected to an amine scrubbing step to remove at least a portion of the $CO_2$ and/or $H_2S$ gas components before being provided to the membrane.

The gas stream may be derived from a renewable feedstock.

The gas stream may be derived from hydrotreatment of a glyceridic feedstock and/or a glycerol-containing feedstock, such as hydrodeoxygenation of a glyceridic feedstock and/or a glycerol-containing feedstock.

The elevated pressure distillation may be conducted at pressures above 20 barg, such as between 25 and 40 barg.

The elevated pressure distillation may be conducted at temperatures above −70° C., such as above 0° C.

The gas stream may contain at least 75 mol-% hydrogen.

The gas stream may contain at least 3 mol-% propane.

The retentate stream may contain less than 65 mol-% hydrogen.

The retentate stream may contain more than 15 mol-% propane, preferably more than 25 mol-% propane.

The propane obtained from the elevated pressure distillation may be formulated into a propane-containing product. The propane-containing product may comprise an odorizing agent.

The hydrogen obtained from the elevated pressure distillation may be combined with the permeate stream and at least partly recycled.

In accordance with the above description, there is also provided a method for treating a hydrotreating reactor outlet gas stream generated from the hydrodeoxygenation and optionally further hydrotreatment of a glyceridic and/or glycerol containing feedstock comprising hydrogen and propane as well as at least one contaminant selected from the group consisting of: $H_2O$, $CO_2$, CO, $H_2S$, $NH_3$ and light hydrocarbons, by elevated pressure distillation separating hydrogen from propane, the method comprising the steps of:
a) providing an elevated pressure distillation unit;
b) positioning upstream of the elevated pressure distillation unit, a membrane separation unit selectively permeable to hydrogen, the membrane separation unit being in connection with the elevated pressure distillation unit such that a retentate stream from the membrane separation unit can pass to the elevated pressure distillation unit;
c) using the membrane separation unit to create a permeate stream enriched in hydrogen and depleted in propane compared with the hydrotreating reactor outlet gas stream, that bypasses the elevated pressure distillation unit, and the retentate stream depleted in hydrogen and enriched in propane compared with the hydrotreating reactor outlet gas stream;
d) using the elevated pressure distillation unit to create a propane rich stream from which hydrogen has been substantially removed and a hydrogen rich stream;
e) optionally recycling and/or combining the permeate stream with the hydrogen rich stream.

BRIEF DESCRIPTION OF DRAWINGS

FIG. 1 shows a scheme illustrating a combination of membrane separation and elevated pressure distillation.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

One of the challenges in preparing renewable fuels from renewable feedstock is the cost associated with the processing. Many renewable fuels involve reactions removing oxygen from the renewable feedstock, and there are a number of strategies for doing this. The deoxygenation reaction(s) result in a number of products, which are further refined into different end-products, such as for example biodiesel.

For example renewable fuel production processes produces a number of by-products besides renewable diesel fuel. A number of these by-products may be recovered, but it cannot always be done in a manner where the efforts of recovering the by-products exceed the value of the by-product, i.e. it is not always feasible often because the energy returned on energy invested (EROEI) is less than or equal to one.

The inventors have found that the combination of a membrane unit with elevated pressure distillation maximise propane and hydrogen recovery in a renewable fuels production unit, and lowers the energy usage, in particular when using glyceridic feedstock, having an abundance of biopropane precursor.

When using glyceridic feedstocks, every glyceridic molecule (e.g. mono-, di-, triglyceridic) will contain a glycerol moiety, which can be converted into biopropane. Propane is currently made from petroleum or recovered from gas fields. Propane is used in the United States for residential heating, and in some countries, including Australia, propane is more widely used as a transportation fuel. Biopropane produced according to the present invention could be used where propane is already used.

Accordingly, here is provided a method for treating a gas stream comprising hydrogen and propane, comprising the steps of: a) providing a membrane having a feed side and a permeate side, the membrane being selective for hydrogen over propane; b) passing the gas stream across the feed side of the membrane; c) withdrawing from the feed side a retentate stream depleted in hydrogen and enriched in propane compared with the gas stream; d) withdrawing from the permeate side a permeate stream enriched in hydrogen and depleted in propane compared with the gas stream; e) subjecting the retentate stream to elevated pressure distillation to separate hydrogen from propane.

The gas stream comprising hydrogen and propane may in various embodiments be derived from a renewable feedstock, i.e. from a feedstock containing some amount of a renewable feedstock as described under the heading Feedstock.

Feedstock

A renewable feedstock refers to a feedstock derived from a biological raw material component containing oils and/or fats containing lipids (e.g. fatty acids or glycerides), such as plant oil/fats, vegetable oil/fats, animal oil/fats, fish oil/fats and algae oil/fats, or oil/fats from other microbial processes, for example genetically manipulated algae oil/fats, genetically manipulated oil/fats from other microbial processes and also genetically manipulated vegetable oil/fats. Components of such materials could also be used, such as for example alkyl esters (typically $C_1$-$C_5$-alkyl esters, such as methyl, ethyl, propyl, iso-propyl, butyl, sec-butyl esters).

These oils and/or fats typically comprise $C_{10}$-$C_{24}$ fatty acids and derivatives thereof, including esters of fatty acids, glycerides, i.e. glycerol esters of fatty acids.

A specific renewable feedstock is a glyceridic feedstock, which is a feedstock that contains glycerides, i.e. one, two or three fatty acids bound to glycerol through ester linkage. The renewable feedstock may also include glycerol. The production of propane from renewable feedstocks is based on the processing of glycerides (i.e. mono-, di-, and tri-glycerides as well as mixtures thereof). Thus, the presence of at least some glycerides within the renewable feedstock is desirable. Feedstock not comprising glycerol or glycerides may also be used, such as fatty acids—here the propane is usually derived from hydrocracking reactions.

The feedstock can include at least 2 wt % of the feedstock being a renewable feedstock, for example at least 5 wt %, at least 25 wt %, at least 50 wt %, at least 75 wt %, at least 90 wt % or at least 95 wt %. The feedstock can also be entirely a feed from a renewable feedstock or it can include 99 wt % or less of the feed being a renewable feedstock, for example 90 wt % or less, 75 wt % or less or 50 wt % or less. With regards to the content of glycerides or glycerol, it is advantageous to have a high amount of renewable feedstock in the feedstock because it potentially includes a greater amount of glycerides or glycerol. Feedstock having lower amounts of renewable feedstock may have other advantages. For example, the catalytic deoxygenation of renewable feedstock is often exothermic, which means that blending the renewable feedstock with a portion that does not contain oxygen or a portion that is not as prone to exothermic reactions during catalytic deoxygenation conditions may be beneficial. Blending may be done for example with feedstock of mineral origin, or may be blended with a recycled product from e.g. catalytic deoxygenation having reduced oxygen content. If a recycled product from catalytic deoxygenation is used in the feedstock, it can correspond to at least 10 wt % of the feedstock being a recycled product, or it can correspond to at least 25 wt %, at least 40 wt %, at least 60 wt %, at least 70 wt %, at least 80 wt % or at least 85 wt %. The recycled product can also correspond to 60 wt % or less, such as 40 wt % or less, or 25 wt % or less.

With regards to a glyceridic or glycerol feedstock, the feedstock can include at least 1 wt % glycerides or glycerol, such as at least 10 wt %, at least 20 wt %, at least 35 wt %, at least 50 wt %, at least 75 wt %, at least 90 wt %. The feedstock can also be composed entirely of glycerides or glycerol or the glyceride/glycerol content can be 95 wt % or less, such as 90 wt % or less, 75 wt % or less, 50 wt % or less, 40 wt % or less, 25 wt % or less. With regards to production of propane or other three carbon molecular species, feedstock having higher glyceride or glycerol contents are preferred. Glyceridic feedstock include triglycerides of $C_{10}$-$C_{28}$ fatty acids, as well as mono- and di-glyceride variants thereof.

Examples of vegetable oils include, but are not limited to rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, tallow oil, and rice bran oil, or fractions of above mentioned oils such as palm olein, palm stearin, purified tall oil, and tall oil fatty acids.

Examples of animal fats include, but are not limited to tallow, lard, yellow grease, brown grease, fish fat, poultry fat.

The gas stream may be derived from hydrotreatment of a feedstock containing some amount of a renewable feedstock as described above, such as for example a glyceridic feedstock. The feedstock may alternatively or additionally contain glycerol, preferably renewable glycerol, which is glycerol obtained from a renewable source. Renewable glycerol is a by-product of the production of fatty acid esters such as for example fatty acid methyl esters (FAME), fatty acid ethyl esters (FAEE) or as a product of fat splitting. Hydrotreatment includes hydrodeoxygenation, which is described below under the heading Removal of oxygen from a renewable feedstock.

Hydrotreatment, e.g. hydrotreatment of glyceride feedstock to renewable fuels, involves various reactions where molecular hydrogen reacts with other components, or components undergo molecular conversions in presence of molecular hydrogen and solid catalyst. The reactions include but are not limited to hydrogenation, hydrodeoxygenation, hydrodesulfurization, hydrodenitrification, hydrodemetallization, hydrocracking and isomerization.

It is preferred that the hydrotreatment conditions are selected such that it provides saturated hydrocarbons.

Removal of Oxygen from a Renewable Feedstock

The preparation of renewable fuels often involve reactions removing oxygen from the renewable feedstock, and there are a number of strategies for doing this. Notably is the hydrodeoxygenation (HDO), which includes three reactions: 1) hydrogenation of oxygen bonds—removing oxygen as $H_2O$, 2) hydrodecarboxylation where oxygen is removed in the form of $CO_2$, and 3) hydrodecarbonylation where oxygen is removed in the form of CO.

However, it is not all renewable fuels that involve removal of oxygen from the renewable feedstock. For example the preparation of fatty-acid methyl ester (FAME) involves transesterification of e.g. glyceride feedstocks, and as such does not remove oxygen (i.e. reduce the oxygen content in the fuel). Glycerol is a by-product of FAME production amounting to approximately 10 wt % of the production of FAME.

Many conditions for hydrodeoxygenation are known to the skilled person. For example the hydrodeoxygenation of a renewable feedstock component can be done on a metal sulphide catalyst. The metal can be one or more Group VI metals, such as Mo or W, or one or more Group VIII non-noble metals such as Co or Ni. The catalyst may be supported on any convenient support, such as alumina, silica, zirconia, titania, amorphous carbon, molecular sieves or combinations thereof. Usually the metal will be impregnated or deposited on the support as metal oxides. They will then typically be converted into their sulphides. Examples of typical catalysts for hydrodeoxygenation are molybdenum containing catalysts, NiMo, CoMo, or NiW catalysts; supported on alumina or silica, but many other hydrodeoxygenation catalysts are known in the art and have been described together with or compared to NiMo and/or CoMo catalysts. The hydrodeoxygenation is typically performed under a hydrogen pressure from 10-200 barg, at temperatures from 200 to 400° C., and liquid hourly space velocities of 0.2 $h^{-1}$ to 10 $h^{-1}$. During the hydrodeoxygenation step the sulfided state of the catalyst is usually maintained by addition of sulphur in the gas phase or by using a feedstock having a sulphur containing mineral oil blended with the renewable feedstock. The sulphur content can be for example 50 wppm to 20000 wppm, usually in the range of 100 wppm to 1000 wppm.

Effective conditions for hydrodeoxygenation may reduce the oxygen content of the feedstock to less than 1 wt %, such as less than 0.5 wt % or less than 0.2 wt %. In some cases the conditions may be selected to yield partial hydrodeoxygenation corresponding to a deoxygenation of at least 40 wt %, at least 50 wt % or at least 75 wt %.

The hydrodeoxygenated product may be separated into a gas stream and a liquid stream. The gas stream comprises hydrogen that has not been used as well as propane. When the renewable feedstock contains triglycerides, propane is obtained mainly from hydrogenation of the glycerol moiety, and to a lesser extent from cracking of the fatty acids.

In various embodiments the gas stream may further comprise at least one further gas chosen from the group consisting of: $H_2O$, $CO_2$, CO, $H_2S$, $NH_3$ and light hydrocarbons. Carbon oxides (CO and $CO_2$) are often present in gas streams from processing of renewable feedstock.

The Gas Stream

After performing hydrodeoxygenation under effective conditions, as described above, propane will usually be present as one of a variety of gas phase components. The hydrodeoxygenated product may be separated into a gas stream and a liquid stream. Besides the hydrogen that has not been used as well as the generated propane, the gas stream can also include, but is not limited to, other hydrodeoxygenation reaction products, such as $H_2S$, as well as $H_2O$, $CO_2$ and CO from the hydrogenation, decarboxylation and decarbonylation reactions, although the amounts will not necessarily represent the extent of these reaction types because of the water-gas shift reaction where CO and $H_2O$ are in equilibrium with $CO_2$ and $H_2$. Additionally there may be light hydrocarbons, for example as a result of cracking, in addition to propane.

The light hydrocarbons include the gaseous light hydrocarbons, i.e. hydrocarbons that are in the gas phase at the pressure and temperature of the gas stream that is to be treated according to the present invention. The light hydrocarbons may for example be hydrocarbons having fewer than seven carbon atoms, i.e. $C_1$-$C_6$ hydrocarbons, which include, but is not limited to: methane, ethane, propane, butane, 2-methylpropane, pentane, isopentane, neopentane, hexane, 2-methylpentane, 3-methylpentane, 2,3-dimethylbutane, 2,2-dimethylbutane. The light hydrocarbons may further be distinguished into light hydrocarbons having a carbon number of 4 or less and light hydrocarbons having a carbon number of 5 or more, e.g. light hydrocarbons having a carbon number of 5-10 or 5-8. In addition to light hydrocarbons, there could also be hydrocarbons having seven or more carbon atoms, for example $C_7$-$C_{10}$ hydrocarbons, but they would normally only be present in a few tens of ppms Hydrogen is usually present in the gas stream as a major component. The gas stream may contain at least 70 mol-% hydrogen, such as at least 75 mol-% hydrogen, at least 80 mol-% hydrogen. The hydrogen content may be less than 95 mol-%, such as less than 90 mol-%.

Propane is also present in the gas stream and the amount depends mainly on the content of triglycerides in the feedstock and to a lesser extent on cracking. The gas stream may contain at least 1 mol-% propane, such as at least 3 mol-% propane. The gas stream may also contain 25 mol-% or less propane, such as 20 mol-% or less, or 15 mol-% or less. When the gas stream is derived from a renewable feedstock the content of the gas stream is often 25 mol-% or less.

In various embodiments the temperature of the gas stream is between 5° C. and 95° C., and the pressure is between 20 barg and 60 barg.

Pre-Treatment of the Gas Stream

Depending on the composition of the gas stream, it may undergo one or more pre-treatment steps before it is passed across the feed side of the membrane. In particular if the gas stream is sour, meaning that it contains $H_2S$, $CO_2$ or both $H_2S$ and $CO_2$, it can undergo sweetening to remove excess $H_2S$ and $CO_2$. The sour gas may be harmful to the membrane material in particular the presence of $H_2S$. The gas stream is considered to be sour, if it contains 5 wppm or more $H_2S$, such as 25 wppm or more, 50 wppm or more, 75 wppm or more, 100 wppm or more. Sweetening of the gas should preferably reduce the $H_2S$ content to 1 wppm or lower, such as 0.5 wppm or lower, or 0.1 wppm or lower.

The gas stream is considered to be sour, if it contains 3000 wppm or more $CO_2$, such as 4000 wppm or more, 5000 wppm or more, 7500 wppm or more. Sweetening of the gas should preferably reduce the $CO_2$ content to 3000 wppm or lower, such as 2000 wppm or lower, or 1000 wppm or lower, or 500 wppm or lower, or 100 wppm or lower, or 10 wppm or lower, such as 1 wppm or lower, and $H_2S$ content to 50 wppm or lower, 10 wppm or lower, 5 wppm or lower, or such as 1 wppm or lower.

The gas may be sweetened using an amine scrubber, or other unit processes used in e.g. refineries, at conditions that reduce or remove both the $H_2S$ and the $CO_2$.

Accordingly, when the gas stream is sour and at least further comprises $CO_2$ and/or $H_2S$, the gas stream may be subjected to a sweetening step, such as an amine scrubbing step, to remove at least a portion of the $CO_2$ and/or $H_2S$ gas components before being provided to the membrane. The amine scrubbing step sweetens the sour gas stream.

Separation of Propane and Hydrogen from the Gas Stream

In order to recover propane from the gas stream, the hydrodeoxygenated product is first separated into the gas stream and a liquid stream. The liquid stream will typically contain hydrocarbons in the diesel boiling range, when biodiesel is produced. The propane and hydrogen from the gas stream comprising hydrogen and propane can then be separated from the remaining gas stream.

In the method for treating the gas stream, treating the gas stream will in various embodiments be separating propane from hydrogen, such as separating both propane and hydrogen from the remaining gas stream.

Step a)

The method involves a step of providing a membrane. The membrane has a feed side and a permeate side. The membrane works by being selective for hydrogen over propane, in that it preferentially permeates hydrogen and rejects propane. When present the one or more of the further gasses chosen from the group consisting of: CO and light hydrocarbons are also rejected together with propane, while $H_2O$, $CO_2$, $H_2S$ and $NH_3$ would be rejected or only partially rejected depending on the membrane type and conditions, e.g. temperature and pressure.

Step b)

In its most basic aspect, the membrane separation involves passing the gas stream containing these components across the feed side of the membrane that is hydrogen selective. A driving force for transmembrane permeation is provided by a higher pressure on the feed side than on the permeate side. For example the pressure on the feed side can include a pressure of 10 barg or higher, such as 20 barg or higher, or 30 barg or higher, or 40 barg or higher, or 50 barg or higher and the pressure on the permeate side can include a pressure that is at least 1 bar lower than the feed side, such as 5 bar or lower, or 10 bar or lower, or 20 bar or lower, or 30 bar or lower. The membrane can be made from polymeric, ceramic or metal materials well known in the art of membrane science, such as cellulose acetate, polysulfone, polyimide, polyamide, zeolite, or palladium, and can be in form of spiral wound membrane, hollow fiber membrane, tube or plate.

Step c)

After membrane separation a retentate stream depleted in hydrogen and enriched in propane compared with the gas stream can be withdrawn from the feed side.

The retentate stream may contain less than 65 mol-% hydrogen, such as less than 55 mol-%, less than 40 mol-%, less than 25 mol-%. The retentate stream may also contain more than 5 mol-% hydrogen, such as more than 10 mol-% hydrogen. The membrane is usually operated such that there will remain some hydrogen in the retentate stream because it will result in a higher purity of hydrogen in the permeate stream.

The retentate stream may also contain more than 15 mol-% propane, for example more than 25 mol-% propane, more than 30 mol-% propane. The retentate stream may also contain less than 75 mol-% propane, such as less than 65 mol-% propane, or less than 55 mol-% propane.

Step d)

After membrane separation a permeate stream enriched in hydrogen and depleted in propane compared with the gas stream can be withdrawn from the permeate side.

In various embodiments the membrane stage cut, defined as the fraction of the gas stream that permeates the membrane may correspond to at least 10%, such as at least 15%, or at least 20%, at least 25%, at least 30%, at least 40%, at least 50%, or at least 75%. The stage cut can also correspond to 95% or less, such as 80% or less, 70% or less, 50% or less. The higher the stage cut, the less pure the hydrogen in the permeate will be. The permeate stream may be used as a recycle hydrogen gas.

Pre-Treatment of the Retentate Stream

The retentate stream will in various embodiments comprise further gas species in addition to propane and hydrogen, which include, but is not limited to $H_2O$, $CO_2$, $H_2S$, $CO$ and other gaseous light hydrocarbons in addition to propane. If the gas is sweet, the further gas species will include, but is not limited to $H_2O$, $CO$ and other gaseous light hydrocarbons in addition to propane.

The retentate stream may be subjected to one or more supplementary treatment steps to remove at least a portion of the further gas species described above before being subjected to the elevated pressure distillation.

The one or more supplementary treatment steps include, but is not limited to: removal of water through e.g. gas drying by adsorption water vapour on a surface, or by absorption on e.g. a dehydrating agent such as glycol or a solid desiccant. Low temperature separation may also be employed to remove water or part of it, as well as some light hydrocarbons, at temperatures below 50° C., such as 40° C. or lower, 30° C. or lower and at temperatures above 5° C.

Step e)

The retentate stream being depleted in hydrogen and enriched in propane compared to the gas stream is subjected to fractionation by distillation, such as cryogenic separation or elevated pressure distillation in order to separate hydrogen from propane. In various embodiments the retentate stream being subjected to the fractionation will be depleted in hydrogen and enriched in propane compared to the gas stream, and further be depleted or have essentially be free of $NH_3$, $H_2O$, $CO_2$ and $H_2S$ and light hydrocarbons. Additionally, in various embodiments the retentate stream being depleted in hydrogen and enriched in propane compared to the gas stream will also comprise further gas species, which includes, but is not limited to $CO$ and $CO_2$ and other gaseous light hydrocarbons in addition to propane.

The elevated pressure distillation is conducted in a pressurised distillation column, where there is a vertical temperature gradient. In various embodiments the elevated pressure distillation could be considered cryogenic separation, in that the elevated pressure distillation may be conducted at temperatures above −100° C., such as above −85° C., above −70° C., such as above 0° C. In various embodiments the temperature range for the distillation column is from 130° C. to −70° C. In various embodiments the bottom of the pressurised distillation column (measured at the valve from which of the column's bottom product is withdrawn) has a temperature of 80° C. to 130° C. The elevated pressure distillation is conducted so as to ensure sufficient theoretical plates so that hydrogen can be separated from propane. In various embodiments where also further gas species are present, which includes, but is not limited to $CO$ and $CO_2$ and other gaseous light hydrocarbons in addition to propane, it is advantageous that conditions are provided to ensure sufficient theoretical plates to separate propane from the further gas species.

In various embodiments the elevated pressure distillation may be conducted at pressures above 20 barg, such as between 25 and 40 barg. The elevated pressure distillation may be performed between −70° C. and 130° C. at such pressures. For example between 0° C. and 130° C.

The propane obtained from the elevated pressure distillation may be formulated into a propane-containing product. The propane-containing product may comprise an odorizing agent, such as for example comprising an odorizing agent selected from one or more of: tert-butylthiol, tetrahydrothiophene and ethanethiol. This product may further be transported to a consumer that could consume the product for example for heating, a fuel for a vehicle, or cooking. In some embodiments of the present invention, the propane obtained from the elevated pressure distillation will with or without further formulation have a minimum of 95% propane and have a maximum of 5% propylene, the remainder being light hydrocarbons, such as iso-butane, butane, ethane, methane. For example the propane obtained may with or without further formulation fulfil one or more of EN 589, DIN 51622, BS 4250 or HD-5 propane specifications. In some embodiments the propane obtained from the elevated pressure distillation does not contain propylene because it is derived from a source that does not contain propylene to start out with, e.g. if conditions for hydrotreatment has been sufficiently severe to ensure that all existing olefins have been hydrogenated and no olefins are formed.

The hydrogen obtained from the elevated pressure distillation may be combined with the permeate stream and at least partly recycled. Alternatively part of the hydrogen obtained from the elevated pressure distillation may be combined with the permeate stream.

Membrane

The membrane is hydrogen selective, in that it selectively permeates hydrogen. Various hydrogen permeable membranes are known in the art, and some of the membranes are based on polymeric, ceramic or metal materials well known in the art of membrane science, such as polysulfone, polyimide, polyamide, cellulose acetate, zeolite or palladium. The membrane may have many different shapes and sizes, such as for example in the form of a spiral wound membrane, hollow fibre membrane, tube membrane or plate membrane. The actual selectivity for hydrogen over propane depends on the material that the membrane is made out of, as well as the process conditions, including the temperature and the pressure on the feed side and the permeate side, respectively.

In various embodiments the membrane material and conditions for membrane separation is chosen so that the membrane being selective for hydrogen over propane exhibit a selectivity for hydrogen over propane of at least 5, such as at least 10, at least 20, at least 30, at least 50, or at least 60 measured as pure component permeability ratio.

In some embodiments a membrane is provided having a feed side and a permeate side, the membrane being selective for hydrogen over propane. A gas stream comprising between 75 and 90 mol % hydrogen and between 5 and 10 mol % propane is being passed across the feed side of the membrane resulting in a retentate gas stream and a permeate gas stream. The retentate gas stream being depleted in hydrogen (between 40 and 60 mol %) and enriched in propane (between 30 and 50 mol %). The permeate gas stream being hydrogen enriched (more than 96 mol %) and depleted in propane (less than 0.5 mol %).

Subjecting then the retentate stream to elevated pressure distillation to further separate hydrogen from pressure yields a combined hydrogen recovery of more than 85 mol %.

Examples of Processing Configurations

In accordance with the above description, there is also provided a method for treating a hydrotreating reactor outlet gas stream generated from the hydrodeoxygenation and optionally further hydrotreatment of a triglyceridic feedstock comprising hydrogen and propane as well as at least one contaminant selected from the group consisting of: $H_2O$, $CO_2$, CO, $H_2S$, $NH_3$ and light hydrocarbons, by elevated pressure distillation separating hydrogen from propane, the method comprising the steps of:

a) providing an elevated pressure distillation unit;
b) positioning upstream of the elevated pressure distillation unit, a membrane separation unit selectively permeable to hydrogen, the membrane separation unit being in connection with the elevated pressure distillation unit such that a retentate stream from the membrane separation unit can pass to the elevated pressure distillation unit;
c) using the membrane separation unit to create a permeate stream enriched in hydrogen and depleted in propane compared with the hydrotreating reactor outlet gas stream, that bypasses the elevated pressure distillation unit, and the retentate stream depleted in hydrogen and enriched in propane compared with the hydrotreating reactor outlet gas stream;
d) using the elevated pressure distillation unit to create a propane rich stream from which hydrogen has been substantially removed and a hydrogen rich stream;
e) optionally recycling and/or combining the permeate stream with the hydrogen rich stream.

FIG. 1 schematically shows an example of a processing configuration suitable for separating propane from hydrogen, and suitable for producing propane. A "pretreated sour hydrogen and propane rich gas stream" is subjected to "Amine wash", which strips $H_2S$ and $CO_2$ from the gas. The "sweet gas" is passed across a membrane and subjected to a "membrane separation", which produces a "permeate hydrogen gas" and a "propane rich gas". The "propane rich gas" is dried to remove water before the "propane rich gas" is taken to the "elevated pressure distillation" step where "propane product" is separated from "hydrogen rich gas with light hydrocarbons and carbon oxide", and "C5+ hydrocarbons".

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments. The terms "comprising", "comprise" and comprises herein are intended by the inventors to be optionally substitutable with the terms "consisting of", "consist of" and "consists of", respectively, in every instance.

The invention claimed is:

1. Method for treating a gas stream comprising hydrogen and propane, comprising the steps of:
   a) providing a membrane having a feed side and a permeate side, the membrane being selective for hydrogen over propane;
   b) passing the gas stream across the feed side of the membrane;
   c) withdrawing from the feed side a retentate stream depleted in hydrogen and enriched in propane compared with the gas stream;
   d) withdrawing from the permeate side a permeate stream enriched in hydrogen and depleted in propane compared with the gas stream;
   e) subjecting the retentate stream to elevated pressure distillation to separate hydrogen from propane, wherein the elevated pressure distillation is conducted at pressures above 20 barg; and
   f) combining the hydrogen obtained from the elevated pressure distillation with the permeate stream, wherein the hydrogen is at least partly recycled.

2. Method according to claim 1, wherein the membrane being selective for hydrogen over propane exhibits a selectivity for hydrogen over propane of at least 5.

3. Method according to claim 1, wherein the gas stream further comprises at least one further gas chosen from the group consisting of: $H_2O$, $CO_2$, CO, $H_2S$, $NH_3$ and light hydrocarbons.

4. Method according to claim 3, wherein the retentate stream is subjected to one or more supplementary treatment steps to remove at least a portion of the at least one further gas before being subjected to the elevated pressure distillation.

5. Method according to claim 3, wherein the gas stream at least further comprises $CO_2$ and $H_2S$, and wherein the gas stream is subjected to an amine scrubbing step to remove at least a portion of the $CO_2$ and $H_2S$ gas components before being provided to the membrane.

6. Method according to claim 1, wherein the gas stream is derived from a renewable feedstock.

7. Method according to claim 6, wherein the gas stream is derived from hydrodeoxygenation of a glyceridic feedstock and/or a glycerol-containing feedstock.

8. Method according claim 1, wherein the elevated pressure distillation is conducted at pressures between 25 and 40 barg.

9. Method according to claim 1, wherein the elevated pressure distillation is conducted at temperatures above −70° C.

10. Method according to claim 1, wherein the gas stream contains at least 75 mol-% hydrogen.

11. Method according to claim 1, wherein the gas stream contains at least 3 mol-% propane.

12. Method according to claim 1, wherein the retentate stream contains less than 65 mol-% hydrogen.

13. Method according to claim 1, wherein the retentate stream contains more than 15 mol-%.

14. Method according to claim 1, wherein the propane obtained from the elevated pressure distillation is formulated into a propane-containing product.

15. Method for treating a hydrotreating reactor outlet gas stream generated from the hydrodeoxygenation and optionally further hydrotreatment of a glyceridic feedstock comprising hydrogen and propane as well as at least one contaminant selected from the group consisting of: $H_2O$, $CO_2$, CO, $H_2S$, $NH_3$ and light hydrocarbons, by elevated pressure distillation separating hydrogen from propane, the method comprising the steps of:
   a) providing an elevated pressure distillation unit;
   b) positioning upstream of the elevated pressure distillation unit, a membrane separation unit selectively permeable to hydrogen, the membrane separation unit being in connection with the elevated pressure distillation unit such that a retentate stream from the membrane separation unit can pass to the elevated pressure distillation unit;

c) using the membrane separation unit to create a permeate stream enriched in hydrogen and depleted in propane compared with the hydrotreating reactor outlet gas stream, that bypasses the elevated pressure distillation unit, and the retentate stream depleted in hydrogen and enriched in propane compared with the hydrotreating reactor outlet gas stream;

d) using the elevated pressure distillation unit to create a propane rich stream from which hydrogen has been substantially removed and a hydrogen rich stream, wherein the elevated pressure distillation is conducted at pressures above 20 barg;

e) recycling and/or combining the permeate stream with the hydrogen rich stream.

16. Method according to claim 1, wherein the elevated pressure distillation is conducted at temperatures above 0° C.

17. Method according to claim 1, wherein the retentate stream contains more than more than 25 mol-% propane.

18. Method according to claim 14, wherein the propane-containing product further comprises an odorizing agent.

* * * * *